United States Patent
Talyansky et al.

(10) Patent No.: US 10,018,608 B2
(45) Date of Patent: Jul. 10, 2018

(54) SYSTEM TO AUTHENTICATE AND IDENTIFY ITEMS

(71) Applicants: Vitaly Talyansky, Portland, OR (US); Edward Talyansky, Battle Ground, WA (US); Jose Gasque, Vancouver, WA (US)

(72) Inventors: Vitaly Talyansky, Portland, OR (US); Edward Talyansky, Battle Ground, WA (US); Jose Gasque, Vancouver, WA (US)

( * ) Notice: Subject to any disclaimer, the term of this patent is extended or adjusted under 35 U.S.C. 154(b) by 0 days.

(21) Appl. No.: 14/634,591

(22) Filed: Feb. 27, 2015

(65) Prior Publication Data

US 2016/0252455 A1 Sep. 1, 2016

(51) Int. Cl.
*G01N 21/64* (2006.01)
*G01N 33/14* (2006.01)
*G01N 21/84* (2006.01)

(52) U.S. Cl.
CPC ......... *G01N 33/14* (2013.01); *G01N 21/6428* (2013.01); *G01N 21/6445* (2013.01); *G01N 2021/6419* (2013.01); *G01N 2021/6441* (2013.01); *G01N 2021/8416* (2013.01)

(58) Field of Classification Search
CPC ....... G01N 21/6486; G01N 2201/0612; C12Q 1/6869
See application file for complete search history.

(56) References Cited

U.S. PATENT DOCUMENTS

| | | | |
|---|---|---|---|
| 6,211,526 B1 * | 4/2001 | Huston | B41M 3/144 250/330 |
| 2003/0003594 A1 * | 1/2003 | Ogura | G01N 21/253 436/172 |
| 2009/0212697 A1 * | 8/2009 | Nakamura | B82Y 30/00 313/506 |
| 2010/0062194 A1 * | 3/2010 | Sun | B42D 25/00 428/29 |
| 2013/0181144 A1 * | 7/2013 | Rapoport | G07D 7/12 250/459.1 |
| 2014/0243934 A1 * | 8/2014 | Vo-Dinh | A61K 49/0039 607/88 |
| 2015/0141267 A1 * | 5/2015 | Rothberg | C12Q 1/6869 506/2 |

* cited by examiner

*Primary Examiner* — David Porta
*Assistant Examiner* — Faye Boosalis (57) ABSTRACT

A system to authenticate and identify items is described herein. An example apparatus includes an illuminating source to illuminate a sample with a first emission of light having a peak wavelength at a first wavelength and a second emission of light having a peak wavelength at a second wavelength, a photo element to detect a first optical response emitted by the sample after the first emission of light and to detect a second optical response emitted by the sample after the second emission of light, and an identifier to identify the sample based on the first optical response and the second optical response.

12 Claims, 4 Drawing Sheets

PHOSPHORS

SAMPLES

| | A | B | C |
|---|---|---|---|
| 1 | X | | |
| 2 | | X | |
| 3 | | | X |
| 4 | X | X | |
| 5 | X | | X |
| 6 | | X | X |
| 7 | X | X | X |

FIG. 4

SYSTEM TO AUTHENTICATE AND IDENTIFY ITEMS

FIELD OF THE DISCLOSURE

The present disclosure relates generally to process control and product authentication and, more particularly, to a product identifier and authenticator.

BACKGROUND

Process control can be improved by detecting that components used in a process are authentic and not counterfeit. Process control can also be improved by automatically identifying the components used in a process and modifying the process accordingly.

DETAILED DESCRIPTION

Process control is an important part of any manufacturing process or other type of process. A manufacturing process often involves the use of many different types of component parts that are each handled differently in the process. In order to fully automate such a manufacturing process, each component part must be identified so that it can be handled properly. Component parts that can be automatically identified can greatly enhance the efficiency of a manufacturing process.

Another potential issue in manufacturing or other processes is counterfeit components. The use of counterfeit components can cause significant economic and other damage to both the purveyor of authentic non-counterfeit components and consumers of products manufactured with counterfeit components. One method to prevent the spread of counterfeit components is to detect counterfeit components before they are used in a process and to take appropriate action to prevent the counterfeit components from being used. Process control can be greatly improved if counterfeit components can be automatically identified as such.

One way to authenticate a component as not being counterfeit is to embed a material in authentic components that can be detected. Authentic components will have this material while counterfeit components will not. Thus, detecting the presence of this material will authenticate the component.

One type of special material that can be used to authenticate components is inorganic ceramic materials known as phosphors. Phosphors have the optical property of luminescence, which is a physical property that manifests in such a way that when a phosphor is illuminated with light at a particular wavelength (the phosphor's excitation wavelength), the phosphors emit light at a different wavelength (the phosphor's emission wavelength). In some phosphors, the excitation wavelength is the same as the emission wavelength. Furthermore, the phosphors can be invisible to the naked eye. Using such a luminescent material as a security feature in a component will make the component difficult to counterfeit.

Phosphors can be used as a security feature in components. A small amount of a particular phosphor can be affixed to or embedded in a component. The component can then be tested for authenticity by illuminating the phosphor with light at the excitation wavelength of the phosphor. If the component has the phosphor affixed to it, the phosphor will luminesce and emit light at the phosphor's emission wavelength that can be detected. If the component does not contain the phosphor, there will be no luminescent emission. Therefore, the component's authenticity can be determined by illuminating the phosphor on the component with light of the appropriate wavelength and detecting whether the component emits light at the expected corresponding wavelength. Furthermore, inorganic ceramics do not interact with the components in which they are embedded, and as such any process that uses components containing phosphors is not impeded in any way through the use of such materials in components.

Another material that can be used to authenticate components is absorbers. When absorbers. When absorbers are illuminated with light at particular wavelengths they absorb part or all of the illuminating light source and reflect the light not absorbed. The amount of light reflected at various wavelengths can be detected. Accordingly, absorbers with known absorption properties can be embedded in components to authenticate the components.

Another material that can be used to authenticate components is film or crystals or other structures that cause a polarity shift in reflected light. Illuminating these materials with un-polarized light will cause the materials to reflect light with a certain polarity. The polarity of the reflected light can be detected. Therefore, materials that polarize light can be used to authenticate components.

In addition to authenticating components by detecting the presence of a particular phosphor or other material in each component, components can be identified by embedding multiple phosphors or other materials in the components. Each type of component can be embedded with a specific combination of phosphors, wherein each phosphor has a different luminescent response. A component can then be tested to determine which phosphors are present in the component and the component can be identified based on the specific mix of phosphors present. Once a component is identified, it can be properly handled. Because this process of authenticating and identifying components is done by illuminating the components with light and detecting a response, it can all be automated.

Another way to identify components using phosphors is to embed several different phosphors in a component in varying amounts. A component can then be tested to determine the amount of each type of phosphor in the component. Different components can be embedded with known amounts of different phosphors to allow for their identification. Alternatively, instead of detecting the exact amount of each type of phosphor in a component, the ratios of different types of phosphors in a component can be detected. Different components can be embedded with known ratios of different phosphors to allow for their identification.

Another way to identify components using phosphors is to embed different amounts or different loading levels of the same phosphor in different components. Then, the amount of phosphor material in a component can be detected and the component can be identified based on this detected amount of phosphor material.

Materials with other optical properties such as absorbers and materials that cause a shift in the polarization of light can also be used to identify components. Different combinations of these materials as well as phosphors can be embedded in a component. For example, a component may be embedded with phosphors with known luminescent properties, absorbers with known absorption properties and crystal with known polarization properties. The component can be identified by detecting the specific luminescent response, absorption rate and polarization response of the component when it is illuminated with light at specific wavelengths. Different components may contain different phosphors, different absorbers, different light polarizing materials or different combinations of all of the above to identify different components.

Example methods, apparatus, and/or articles of manufacture disclosed herein provide a system to authenticate and identify products. In particular, examples disclosed herein provide a mechanism for determining if an item is authentic and identifying the item by illuminating the item with light at one or more wavelengths and detecting the luminescent or other optical response to each of the illuminating wavelengths.

In examples disclosed herein, phosphor materials having one or more known luminescent or other optical responses are embedded in a sample. In examples disclosed herein, an authenticator illuminates a sample with light at one or more wavelengths. In examples disclosed herein, the authenticator detects the luminescent response from the sample after illumination of the sample by each wavelength of light. In examples disclosed herein, the authenticator identifies the sample based on the detected luminescent or other optical response. In examples disclosed herein, a process controller takes one or more actions based on the identification of the sample.

In some examples disclosed herein, different phosphor materials are spatially located in different areas of an item. In these examples, each phosphor location is illuminated with light at an appropriate wavelength to cause a luminescent response by a particular type of phosphor material. In these examples, the luminescent or other optical response from each location is detected and the sample is identified based on which spatial locations of the item contain each type of phosphor material.

In examples disclosed herein, absorbers having known absorption properties are embedded in a sample. In examples disclosed herein, an authenticator illuminates a sample containing certain absorbers with light at one or more wavelengths. In examples disclosed herein, the authenticator detects the amount of light reflected by the sample after illumination of the sample by each wavelength of light. In examples disclosed herein, the authenticator identifies the sample based on the detected absorption of the sample.

In some examples disclosed herein, materials with known polarization properties are embedded in a sample. In examples disclosed herein, an authenticator illuminates a sample containing certain optical polarizing materials with light at one or more wavelengths. In examples disclosed herein, the authenticator detects the polarization of light reflected by the sample after illumination of the sample by each wavelength of light. In examples disclosed herein, the authenticator identifies the sample based on the detected polarization properties of the sample. In examples disclosed herein, a process controller takes one or more actions based on the identification of the sample.

Figure 1:
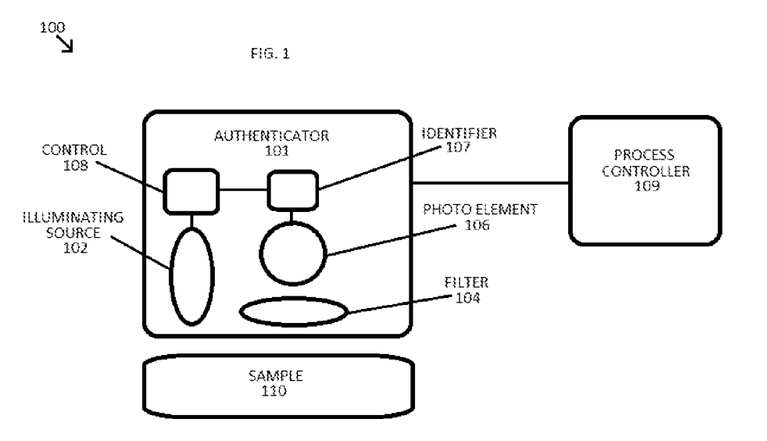
FIG. 1 is a block diagram of an example system to authenticate and identify items constructed in accordance with the teachings of this disclosure.

FIG. 1 is a block diagram of an example system 100 to authenticate and identify items. The example of FIG. 1 includes an authenticator 101, a process controller 109 and a sample 110. The example authenticator 101 includes an illuminating source 102, a filter 104, a photo element 106, an identifier 107 and a control 108.

The example illuminating source 102 of FIG. 1 illuminates the example sample 110 with light or other electromagnetic radiation having a wavelength that causes the sample 110 to luminesce or emit another optical response that can be detected such as a shift in the polarity of reflected light or an absorption of certain wavelengths of light. In the illustrated example, the illuminating source 102 emits light at multiple wavelengths. In other examples, the illuminating source 102 consists of multiple sources that each emit light or other electromagnetic radiation at a different wavelength. In the illustrated example, the illuminating source 102 is a light emitted diode (LED). In other examples, the illuminating source 102 may be a laser or any other source capable of emitting electromagnetic radiation at the appropriate wavelength or wavelengths to cause a luminescent or other optical response by the sample 110.

The example filter 104 of FIG. 1 is an optical filter that passes certain types of light and blocks other types of light. In the illustrated example, the filter 104 passes the light emitted by the example sample 110 but blocks the emission from the example illuminating source 102. In the illustrated example, when the sample 110 is illuminated with light at a particular wavelength, the sample 110 luminesces and emits light at a different wavelength. The difference between the wavelength of light that causes the luminescence in the example sample 110 (the excitation wavelength) and the wavelength of light emitted by the sample 110 (the emission wavelength) is known as the Stokes shift. After the example illuminating source 102 in the example authenticator 101 emits light to trigger luminescence by the example sample 110, the luminescent emission of the sample 110 illuminates the front of the authenticator 101. However, the reflection or other propagation of light from the illuminating source 102 may also illuminate the authenticator 101. Therefore, the example filter 104 is needed to filter out the light from the example illuminating source 102 so that the example photo element 106 will only detect the luminescent emission from the example sample 110 and not the emission from the illuminating source 102.

In the illustrated example, the illuminating source 102 emits light at multiple wavelengths. Therefore, the example filter 104 blocks light at each of the wavelengths of emitted by the example illuminating source 102. In the illustrated example, the luminescent emission of the sample 110 has a higher wavelength than any of the wavelengths of light emitted by the illuminating source 102. Therefore, in the illustrated example, the filter 104 is a high-pass filter (i.e., the filter 104 only passes light with a wavelength above a certain wavelength). In other examples, the luminescent emission of the sample 110 may have a lower wavelength than the wavelengths of light emitted by the illuminating source 102. In these examples, the filter 104 is a low-pass filter (i.e., the filter 104 only passes light with a wavelength below a certain wavelength). In other examples, a band-pass filter allowing only certain wavelengths through the filter 104 is used.

In some examples, the excitation wavelength emitted by the illuminating source 102 is the same as the emission wavelength emitted by the sample 110. In these examples, the filter 104 may not be present. In these examples, the illuminating source 102 is turned on to emit light and trigger a luminescent response in the sample 110. The example illuminating source 102 is then turned off before the luminescent response emitted by the example sample 110 is detected.

In some examples, the optical response of the sample 110 to illumination by the illuminating source 102 that is detected is a shift in the polarity of the light reflected by the sample 110. In these examples, the filter 104 is a polarizing filter that only passes light polarized in a manner that the sample 110 polarizes the light emitted by the illuminating source 102.

The example photo element 106 detects the light emitted from the example sample 110 after it passes through the example filter 104. In the illustrated example, the photo element 106 is a photo-diode that detects light at each of the wavelengths emitted by the sample 110. In other examples, the photo element 106 may be any device capable of detecting the emission of light by the sample 110. In some examples, the photo element 106 may consist of multiple photo-diodes that each detect light at a particular wavelength.

The example identifier 107 authenticates and identifies the sample 110. In the illustrated example, the identifier 107 determines whether the photo element 106 has detected a luminescent response after the illuminating source 102 illuminates the sample 110 with light at a particular wavelength. The example identifier 107 makes this determination after each such illumination of the example sample 110 by the example illuminating source 102 and stores the result of this determination. After the example illuminating source 102 has illuminated the example sample 110 with light at each of the desired wavelengths and the example identifier 107 has determined whether the example photo element 106 detected a luminescent response to each of the various wavelengths, the identifier 107 determines if the sample 110 is authentic and identifies the sample 110 based on which wavelengths of light emitted by the illuminating source 102 caused the sample 110 to emit a luminescent response. In some examples, the identifier 107 determines whether the sample 110 is authentic based on the shift in polarity of light reflected by the sample 110. In other example identifier 107 determines whether the sample is authentic based on the absorption of light by the sample 110.

The example control 108 controls the example illuminating source 102 and the example identifier 107. In the illustrated example, the control 108 determines which wavelength of light is to be emitted by the illuminating source 102 and causes the illuminating source 102 to emit light at the appropriate wavelength for a certain amount of time. In addition, the example control 108 communicates with the example identifier 107 and transmits to the identifier 107 which wavelength of light is being emitted by the example illuminating source 102. This allows the example identifier 107 to determine which wavelengths of light cause a luminescent response in the example sample 110.

The example sample 110 is a component, product, or any item or device that is to be authenticated and identified. In the illustrated example, the sample 110 is embedded with one or more types of phosphor materials, wherein each type of phosphor has a different luminescent response. In the illustrated example, each type of phosphor embedded in the sample 110 has a unique luminescent response and emits light at a particular wavelength when it is illuminated with light at a different wavelength. In some examples, the sample 110 is embedded with one or more phosphors in varying known amounts. In some examples, the sample 110 is embedded with one or more types of absorbers that absorb a known amount of light at certain wavelengths. In some examples, the sample 110 is embedded with materials that change the polarization of light. In some examples, the sample 110 is embedded with a combination of different phosphors, absorbers and materials that change the polarization of light.

The example process controller 109 controls a manufacturing process or other process in which the example sample 110 is used. In the illustrated example, the process controller 109 is connected to and communicates with the authenticator 101. In other examples, the process controller 109 may communicate with the authenticator 101 wirelessly, via the internet, via a network, or via other means. In the illustrated example, the authenticator 101 communicates to the process controller 109 whether the sample 110 is authentic, and if so, the identity of the sample 110. The example process controller 109 modifies the process it is controlling based on whether the sample 110 is authentic and based on the identification of the example sample 110.

In the illustrated example, the authenticator 101 is part of a manufacturing process. In the illustrated example, the sample 110 is a component that is used in the manufacturing process and the process controller 109 controls one or more aspects of the manufacturing process. In the illustrated example, the authenticator 101 determines if the sample 110 is authentic and if so, what type of component it is. In the illustrated example, the process controller 109 modifies the manufacturing process based on the determination made by the authenticator 101. In the illustrated example, if the authenticator 101 determines that the sample 110 is not authentic, the process controller 109 will not use the sample 110 in the manufacturing process and will alert an individual that a non-authentic component has been detected. In the illustrated example, if the authenticator 101 determines that the sample 110 is authentic, the process controller 109 modifies the manufacturing process based on the identification of the sample 110. This modification of the manufacturing process by the example process controller 109 may involve sending the example sample 110 to a specific point on an assembly line to be used or may involve performing a certain action to or with the sample 110.

In other examples, the authenticator 101 is used in a coffee maker. In these examples, the sample 110 is a single-serve coffee pod containing a specific flavor of coffee and the process controller 109 controls the process of brewing the coffee in the pod by the coffee maker. In these examples, the process controller 109 will not brew coffee if the coffee filter (the sample 110) is determined not to be authentic. Also in these examples, if the coffee pod is determined to be authentic, the process controller 109 brews the coffee differently depending on the identification of the coffee pod by the authenticator 101. For example, the process controller 109 may change the temperature of the coffee maker or the duration of the brewing time based on the type of coffee pod detected by the authenticator 101. This allows for automatic custom brewing of different types and flavors of coffee.

In other examples, the system 100 is used in conjunction with medical devices. In these examples, the sample 110 is a medical device and the authenticator 101 determines the authenticity and type of medical device. In these examples, if the authenticator 101 determines that the sample 110 is not authentic, the process controller 109 alerts a doctor or nurse or other staff member of the medical device's inauthenticity. Also in these examples, if the authenticator 101 determines that the sample 110 is not the appropriate medical device for a particular patient, the process controller 109 alerts a doctor or nurse. Further, in these examples, after the sample 110 is identified as a particular medical device, the process controller 109 may adjust certain settings of other devices that are used in conjunction with the medical device identified by the authenticator 101.

In other examples, the sample 110 may be any item used in any type of process. The example authenticator 101 may be used to authenticate and identify any item used in a process. And the example process controller 109 may be used to control any type of process that utilizes the example sample 110.

While an example manner of implementing the system to authenticate and identify items has been illustrated in FIG. 1, one or more of the elements, processes and/or devices illustrated in FIG. 1 may be combined, divided, re-arranged, omitted, eliminated and/or implemented in any other way. Further, the example authenticator 101, the example illuminating source 102, the example filter 104, the example photo element 106, the example identifier 107, the example control 108, the example process controller 109 and/or, more generally, the system to authenticate and identify documents 100 of FIG. 1 may be implemented by hardware, software, firmware and/or any combination of hardware, software and/or firmware. Thus, for example, any of the example authenticator 101, the example illuminating source 102, the example filter 104, the example photo element 106, the example identifier 107, the example control 108, the example process controller 109 and/or, more generally, the system to authenticate and identify documents 100 of FIG. 1 could be implemented by one or more circuit(s), programmable processor(s), application specific integrated circuit(s) (ASIC(s)), programmable logic device(s) (PLD(s)), microprocessor(s), hardware processor(s), and/or field programmable logic device(s) (FPLD(s)), etc. When any of the system or apparatus claims of this patent are read to cover a purely software and/or firmware implementation, at least one of the example authenticator 101, the example illuminating source 102, the example filter 104, the example photo element 106, the example identifier 107, the example control 108, the example process controller 109 and/or, more generally, the system to authenticate and identify documents 100 of FIG. 1 is hereby expressly defined to include a tangible computer readable storage medium such as a memory, DVD, CD, Blu-ray, etc. storing the software and/or firmware. Further still, the example authenticator 101, the example illuminating source 102, the example filter 104, the example photo element 106, the example identifier 107, the example control 108, the example process controller 109 and/or, more generally, the system to authenticate and identify documents 100 of FIG. 1 may include more than one of any or all of the illustrated elements, processes and devices.

Figure 2:
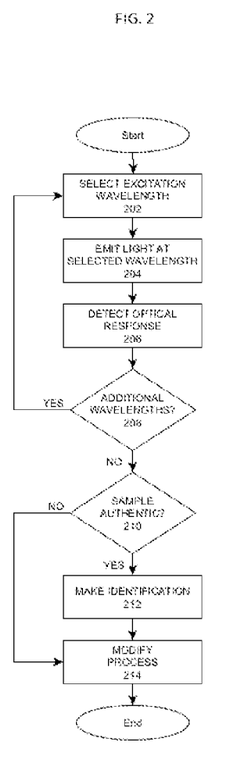
FIG. 2 is a flowchart representative of example machine readable instructions that may be executed to implement the example system of FIG. 1.

FIG. 2 is a flowcharts representative of example machine readable instructions for implementing the example system to authenticate and identify items 100 of FIG. 1. In the example flowchart of FIG. 2, the machine readable instructions comprise program(s) for execution by a processor such as the processor 412 shown in the example computer 400 discussed below in connection with FIG. 4. The program(s) may be embodied in software stored on a tangible computer readable storage medium such as a CD-ROM, a floppy disk, a flash drive, a hard drive, a digital versatile disk (DVD), a Blu-ray disk, or a memory associated with the processor 412, but the entire program and/or parts thereof could alternatively be executed by a device other than the processor 412 and/or embodied in firmware or dedicated hardware. Further, although the example program(s) is described with reference to the flowchart illustrated in FIG. 2, many other methods of implementing the example system to authenticate and identify items 100 of FIG. 1 may alternatively be used. For example, the order of execution of the blocks may be changed, and/or some of the blocks described may be changed, eliminated, or combined.

As mentioned above, the example processes of FIG. 2 may be implemented using coded instructions (e.g., computer readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage media in which information is stored for any duration (e.g., for extended time periods, permanently, brief instances, for temporarily buffering, and/or for caching of the information). As used herein, the term tangible computer readable storage medium is expressly defined to include any type of computer readable storage device and/or disk and to exclude propagating signals. Additionally or alternatively, the example processes of FIG. 2 may be implemented using coded instructions (e.g., computer readable instructions) stored on a non-transitory computer readable medium such as a hard disk drive, a flash memory, a read-only memory, a compact disk, a digital versatile disk, a cache, a random-access memory and/or any other storage media in which information is stored for any duration (e.g., for extended time periods, permanently, brief instances, for temporarily buffering, and/or for caching of the information). As used herein, the term non-transitory computer readable storage medium is expressly defined to include any type of computer readable storage device and/or disk and to exclude propagating signals. As used herein, when the phrase "at least" is used as the transition term in a preamble of a claim, it is open-ended in the same manner as the term "comprising" is open ended. Thus, a claim using "at least" as the transition term in its preamble may include elements in addition to those expressly recited in the claim.

FIG. 2 begins when the example control 108 selects a wavelength of light to emit onto the example sample 110 (block 202). The wavelength selected in block 202 is equal to the excitation wavelength of one of the phosphor materials in the example sample 110.

After the example control 108 selects a wavelength of light to emit onto the example sample 110 (block 202), the control 108 sends a signal to the example illuminating source 102 and the illuminating source 102 emits light at the selected wavelength onto the example sample 110 (block 204). In the illustrated example, the illuminating source 102 emits light at the specified wavelength for a specified duration of time long enough to cause an optical response in the example sample 110 that can be detected by the example photo element 106. In some examples, the illuminating source 102 emits light at the selected wavelength in a series of short pulses. In the illustrated example, after the illuminating source 102 emits light at the specified wavelength for the specified time, the illuminating source 102 stops emitting light.

When the example sample 110 is illuminated by the example illuminating source 102, if any phosphors are present in the sample 110 that have an excitation wavelength equal to the wavelength of light emitted by the illuminating source 102, the sample 110 emits light at the emission wavelength of the excited phosphors. In the illustrated example, this luminescent emission passes through the example filter 104 and is then detected by the example photo element 106 (block 206). If there is no phosphor material embedded in the example sample 110 with the appropriate excitation wavelength, then no luminescent response will be emitted by the example sample 110 or detected by the example photo element 106. The result of whether a luminescent response is detected by the example photo element 106 after the example sample 110 is illuminated by the selected wavelength is stored by the example identifier 107. In the illustrated example, the photo element 106 only detects whether or not a luminescent response is present. In other examples, the photo element 106 detects the strength of the luminescent response from the sample 110, which corresponds to the amount of a certain type of phosphor material in the sample 110. In some examples, the photo element 106 detects the strength of the reflection from the sample 110, which corresponds to the type of absorbers in the sample 110. In some examples, the photo element 106 detects the strength of the reflection from the sample 110 after the reflection passes through a polarizing filter 104, which corresponds to the polarization properties of the sample 110. In all of these examples, whatever information is detected by the identifier 107 is stored by the identifier 107.

After the example photo element 106 detects whether there is an optical response emitted by the example sample 110, the example control 108 determines whether light with additional wavelengths is to be emitted onto the sample 110 (block 208). This determination is made by comparing the wavelengths of light that have already been emitted to all of the wavelengths to be emitted onto the example sample 110. In the illustrated example, the sample 110 contains various phosphor materials that each have a unique excitation wavelength. After the block diagram of FIG. 2 is finished executing, all of these excitation wavelengths must have been emitted by the example illuminating source 102 in order to properly identify the example sample 110. Therefore, in block 208 of FIG. 2, the example control determines whether any of these wavelengths of light have not yet been emitted by the example illuminating source 102.

If the example control 108 determines that additional wavelengths of light need to be emitted by the example illuminating source 102 (block 208), then control returns to block 202 and the control 108 selects another wavelength. If the example control 108 determines that additional wavelengths of light do not need to be emitted by the example illuminating source 102 (block 208), then control passes to block 210.

If the example control determines that no additional wavelengths of light need to be emitted by the example illuminating source 102 onto the example sample 110 (block 208), then the example identifier 107 determines whether the example sample 110 is authentic (block 210). In the illustrated example, the identifier 107 determines that the sample 110 is authentic if the photo element 106 detected a luminescent response from the sample 110 after illumination by the illuminating source 102 at any wavelength. In the illustrated example, if there was no luminescent response detected by the example photo element 106 from illumination of the example sample 110 by any wavelength of light, then the example identifier 107 determines that there is no phosphor material in the sample 110 and that the sample 110 is not authentic. In some examples, the identifier 107 determines that the sample 110 is authentic only if a luminescent response is detected by the photo element 106 after illumination of the sample 110 by certain wavelengths of light from the illuminating source 102. In some examples, the identifier 107 determines whether the sample 110 is authentic based on the reflection from the sample 110 detected by the photo element 106 after illumination of each wavelength of light by the illuminating source 102, which corresponds to the type of absorbers or light polarizing materials in the sample 110.

If the example identifier 107 determines that the example sample 110 is not authentic (block 210), then control passes to block 214. If the example identifier 107 determines that the example sample 110 is authentic (block 210), then the identifier 107 identifies the sample 110 (block 212). In the illustrated example, the identifier 107 identifies the sample 110 based on the combination of wavelengths emitted by the example illuminating source 102 that caused a luminescent response to be emitted by the sample 110.

Figure 3:
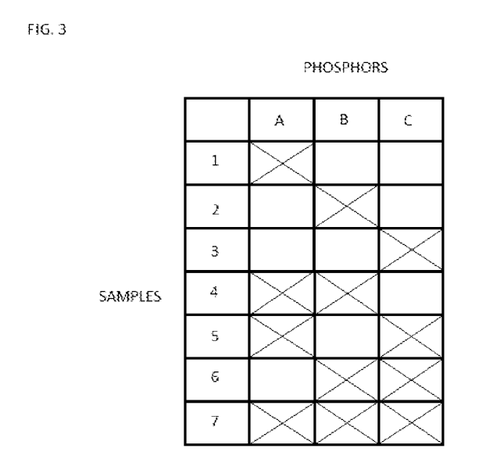
FIG. 3 is an example illustration of how different phosphor materials can be included in a sample to identify the sample.

In the illustrated example, each type of sample 110 that is to be identified contains a unique mix of phosphor materials with unique luminescent responses. In the illustrated example, each sample 110 contains up to three different phosphor materials as shown in FIG. 3. In other examples, each sample 110 may contain any number of phosphor materials. In the example of FIG. 3, each sample may contain or may not contain phosphor materials A, B and/or C. Each phosphor material A, B and C has a different luminescent response that can be detected by the example authenticator 101. In the example of FIG. 3, sample 1 contains phosphor material A but does not contain phosphor materials B or C. In the example of FIG. 3, sample 2 contains phosphor material B but does not contain phosphor materials A or C. In the example of FIG. 3, sample 3 contains phosphor material C but does not contain phosphor materials A and B. In the example of FIG. 3, sample 4 contains phosphor materials A and B but does not contain phosphor material C. In the example of FIG. 3, sample 5 contains phosphor materials A and C but does not contain phosphor material B. In the example of FIG. 3, sample 6 contains phosphor materials B and C but does not contain phosphor material A. In the example of FIG. 3, sample 7 contains phosphor materials A, B and C. In the example of FIG. 3, a non-authentic sample would not contain phosphor materials A, B or C. In other examples, the samples contain a mix of absorbers with different absorption properties, light polarizing materials with different polarization properties or a combination of phosphors, absorbers and light polarizing materials.

In the illustrated example, the identifier 107 determines the identity of the sample 110 by comparing the phosphor materials detected in block 206 to the chart in FIG. 3. For example, if phosphor materials A and B were detected in the sample 110, then the sample 110 must be sample 4. If only phosphor material C was detected, then the example sample 110 must be sample 3. In other examples, any number and combination of phosphor materials can be used to create any number of identifiable samples.

In some examples, the photo element 106 detects the amount of each type of phosphor material embedded in the sample 110 based on the strength of the luminescent responses detected in block 206. In these examples, different samples may contain not only different types of phosphor materials but different amounts of certain phosphor materials in known quantities. In these examples, the identifier 107 identifies the sample 110 based on the amount of each type of phosphor material in the sample 110. In other examples, the identifier 107 identifies the sample 110 based on the ratio of each type of phosphor material in the sample 110. For example, one sample may have an equal amount of phosphor materials A and B whereas another sample may have twice as much of phosphor material A as phosphor material B.

In some examples, each type of sample contains only one phosphor material in varying amounts. In these examples, the illuminating source 102 only emits light at one wavelength corresponding to the excitation wavelength of the phosphor material in the various samples. In these examples, the photo element 106 determines the strength of the luminescent response emitted by the sample 110 in response to illumination by the light emitted by the illuminating source 102. In these examples, the identifier 107 identifies the sample 110 based on the strength of the luminescent response detected by the photo element 106.

After the example identifier 107 determines that the example sample 110 is not authentic (block 210) or after the identifier 107 identifies the sample 110 (block 212), the example process controller 109 modifies the process based on the identity of the sample 110 (block 214). The example process controller 109 can modify the process in any number of ways depending on the particular process in which the system 100 is being used. In some examples, if the sample 110 is determined to be not authentic, the process controller 109 alerts an appropriate individual. In some examples, the process controller 109 causes a modification of the sample 110 based on the identification of the sample 110. In some examples, the process controller 109 performs different actions depending on the identity of the sample 110. The example process controller 109 can modify a process in any way based on the identification of the sample 110 and the determination of whether the sample 110 is authentic. The example of FIG. 2 then ends.

Figure 4:
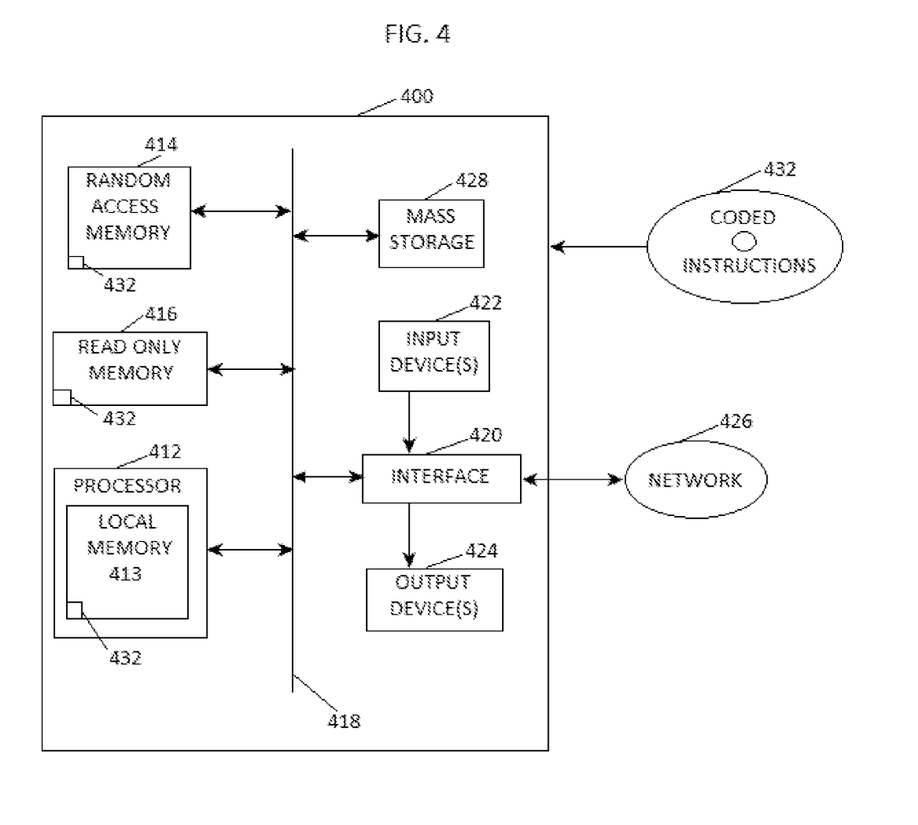
FIG. 4 is a block diagram of an example processing system capable of executing the example machine readable instructions of FIG. 2 to implement the example system of FIG. 1.

FIG. 4 is a block diagram of a processor platform 400 capable of executing the instructions of FIG. 2 to implement the system to authenticate and identify items 100 of FIG. 1. The processor platform 400 can be, for example, a server, a personal computer, an Internet appliance, a DVD player, a CD player, a Blu-ray player, a gaming console, a personal video recorder, a smart phone, a tablet, a printer, or any other type of computing device.

The processor platform 400 of the instant example includes a processor 412. As used herein, the term "processor" refers to a logic circuit capable of executing machine readable instructions. For example, the processor 412 can be implemented by one or more microprocessors or controllers from any desired family or manufacturer.

The processor 412 includes a local memory 413 (e.g., a cache) and is in communication with a main memory including a volatile memory 414 and a non-volatile memory 416 via a bus 418. The volatile memory 414 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 416 may be implemented by flash memory and/or any other desired type of memory device. Access to the main memory 414, 416 is controlled by a memory controller.

The processor platform 400 also includes an interface circuit 420. The interface circuit 420 may be implemented by any type of interface standard, such as an Ethernet interface, a universal serial bus (USB), and/or a PCI express interface.

One or more input devices 422 are connected to the interface circuit 420. The input device(s) 422 permit a user to enter data and commands into the processor 412. The input device(s) can be implemented by, for example, a keyboard, a mouse, a touchscreen, a track-pad, a trackball, isopoint and/or a voice recognition system.

One or more output devices 424 are also connected to the interface circuit 420. The output devices 424 can be implemented, for example, by display devices (e.g., a liquid crystal display, a cathode ray tube display (CRT), a printer and/or speakers). The interface circuit 420, thus, typically includes a graphics driver card.

The interface circuit 420 also includes a communication device such as a modem or network interface card to facilitate exchange of data with external computers via a network 426 (e.g., an Ethernet connection, a digital subscriber line (DSL), a telephone line, coaxial cable, a cellular telephone system, etc.).

The processor platform 400 also includes one or more mass storage devices 428 for storing software and data. Examples of such mass storage devices 428 include floppy disk drives, hard drive disks, compact disk drives and digital versatile disk (DVD) drives.

The coded instructions 432 of FIG. 4 may be stored in the mass storage device 428, in the volatile memory 414, in the non-volatile memory 416, and/or on a removable storage medium such as a CD or DVD.

Although certain example apparatus, methods, and articles of manufacture have been disclosed herein, the scope of coverage of this patent is not limited thereto. On the contrary, this patent covers all apparatus, methods, and articles of manufacture fairly falling within the scope of the claims of this patent.

What is claimed is:

1. A system comprising:
   an illuminating source to illuminate a sample with light at a first wavelength, the sample containing inorganic ceramic phosphor material and having a first optical response when it is illuminated by light at the first wavelength;
   a photo element to detect the first optical response;
   an identifier to determine a first identity of the sample based on the first optical response and
   a process controller to control a process for brewing coffee, wherein the process controller modifies the process based on the first identity.

2. The system of claim 1, wherein the first optical response is a luminescent response such that the sample emits light at a second wavelength when it is illuminated by light at a first wavelength.

3. The system of claim 1, wherein the sample further contains absorbers that absorb light at a second wavelength when the sample is illuminated by light at a third wavelength.

4. The system of claim 1, wherein the sample reflects light having a second polarity when it is illuminated light having a first polarity such that the first polarity and the second polarity are different.

5. The system of claim 1, wherein the first wavelength is in the infrared portion of the electromagnetic spectrum.

6. A method comprising:
   illuminating a sample with light at a first wavelength, the sample containing inorganic ceramic phosphor material and having a first optical response when it is illuminated by light at the first wavelength;
   detecting the first optical response;
   determining a first identity of the sample based on the first optical response; and
   modifying a process for brewing coffee based on the first identity.

7. The method of claim 6, wherein the first optical response is a luminescent response such that the sample emits light at a second wavelength when it is illuminated by light at a first wavelength.

8. A system comprising:
- an illuminating source to illuminate a sample with light at a first wavelength, the sample containing inorganic ceramic phosphor material and having a first optical response when it is illuminated by light at the first wavelength;
- a photo element to detect the first optical response;
- an identifier to determine a first identity of the sample based on the first optical response; and
- a process controller to control the operation of a medical device and to create a first alert when the first identity is different from an expected identity.

9. The system of claim 8, wherein the first optical response is a luminescent response such that the sample emits light at a second wavelength when it is illuminated by light at a first wavelength.

10. The system of claim 8, wherein the sample further contains absorbers that absorb light at a second wavelength when the sample is illuminated by light at a third wavelength.

11. The system of claim 8, wherein the sample reflects light having a second polarity when it is illuminated light having a first polarity such that the first polarity and the second polarity are different.

12. The system of claim 8, wherein the first wavelength is in the infrared portion of the electromagnetic spectrum.

* * * * *